US012083032B2

(12) United States Patent
Loidl et al.

(10) Patent No.: US 12,083,032 B2
(45) Date of Patent: Sep. 10, 2024

(54) DEVICE FOR SUPPORTING AT LEAST ONE ARM OF A USER, AND HEADREST

(71) Applicant: Ottobock SE & Co. KGAA, Duderstadt (DE)

(72) Inventors: Maximilian Loidl, Reit im Winkel (DE); Lisa Michalke, Siegsdorf (DE); Andreas Zehetmaier, Schnaitsee (DE); Robert Wagner, Trostberg (DE); Klaus Mader, Waging (DE); Valentin Illenseer, Grassau (DE); Sebastian Muck, Traunstein (DE); Bruno Kapeller, Siegsdorf (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 153 days.

(21) Appl. No.: 17/432,872

(22) PCT Filed: Feb. 19, 2020

(86) PCT No.: PCT/EP2020/054372
§ 371 (c)(1),
(2) Date: Aug. 20, 2021

(87) PCT Pub. No.: WO2020/169674
PCT Pub. Date: Aug. 27, 2020

(65) Prior Publication Data
US 2022/0117767 A1  Apr. 21, 2022

(30) Foreign Application Priority Data
Feb. 20, 2019 (DE) .......................... 102019104344.1

(51) Int. Cl.
*A61F 5/01* (2006.01)

(52) U.S. Cl.
CPC ...... *A61F 5/013* (2013.01); *A61F 2005/0144* (2013.01); *A61F 2005/0167* (2013.01)

(58) Field of Classification Search
CPC .. A61F 5/00; A61F 5/01; A61F 5/0102; A61F 5/0118; A61F 5/013; A61F 5/055;
(Continued)

(56) References Cited

U.S. PATENT DOCUMENTS 3,945,376 A    3/1976  Kuehnegger
5,470,890 A *  11/1995 House ................ C08G 18/3234
                                                      528/68
(Continued)

FOREIGN PATENT DOCUMENTS

AT        007850 U1   10/2005
CN       202605212 U  12/2012
(Continued)

OTHER PUBLICATIONS

International Search Report issued in PCT/EP2020/054372, dated May 28, 2020, 2 pgs.
(Continued)

*Primary Examiner* — Ophelia A Hawthorne
*Assistant Examiner* — Gina McCarthy
(74) *Attorney, Agent, or Firm* — HOLLAND & HART LLP

(57) ABSTRACT

The invention relates to a device for supporting at least one arm of a user, with at least one arm support element with a spacer element and an arm shell for mounting on the upper arm, at least one passive actuator which is configured to apply a force to the arm support element, and at least one counter bearing for the force to be applied that comprises at least one force transmission element and a counter bearing element, wherein the spacer element is arranged on the at least one force transmission element such that it can be (Continued)

swivelled, a headrest with at least one shoulder element and at least one support element that is arranged on the at least one shoulder element, wherein the headrest is designed to support the user's head.

18 Claims, 7 Drawing Sheets

(58) Field of Classification Search
CPC .............. A61F 5/05841; A61F 5/05858; A61F 5/05883; A61F 5/37; A61F 5/3707; A61F 5/3715; A61F 5/3723; A61F 2005/0144; A61F 2005/0132; A61F 2005/0134; A61F 2005/0165; A61F 2005/0167; A61G 7/05; A61G 7/065; A61G 7/07; A61G 7/072; A61B 6/0407; A61B 6/0421; A61B 2090/101; A61B 90/53; A61N 2005/1097; B25J 9/0006; A61H 1/0274; A61H 1/0281; A41D 13/0512; C08G 18/3234
See application file for complete search history.

(56) References Cited

U.S. PATENT DOCUMENTS

| | | | |
|---|---|---|---|
| 5,531,669 A | 7/1996 | Varnau | |
| 6,308,345 B1 * | 10/2001 | Williams, Jr. | A41D 13/0512 |
| | | | 602/17 |
| 2005/0283884 A1 | 12/2005 | Poole | |
| 2014/0033391 A1 * | 2/2014 | Doyle | A61B 90/53 |
| | | | 2/16 |
| 2014/0158839 A1 | 6/2014 | Doyle | |
| 2016/0325428 A1 | 11/2016 | Chun | |
| 2017/0173783 A1 | 6/2017 | Angold | |
| 2019/0015237 A1 | 1/2019 | Agrawal et al. | |
| 2019/0290468 A1 * | 9/2019 | Briant | A41D 13/0512 |

FOREIGN PATENT DOCUMENTS

| | | | |
|---|---|---|---|
| CN | 106112962 A | 11/2016 | |
| DE | 3423872 A1 | 10/1983 | |
| DE | 20304977 U1 | 5/2004 | |
| DE | 60015545 T2 | 3/2005 | |
| DE | 102016104880 A1 | 9/2017 | |
| FR | 3019973 A1 | 4/2018 | |
| KR | 20080107225 A | 12/2008 | |
| WO | 2017157875 A1 | 9/2017 | |
| WO | 2018224175 A1 | 12/2018 | |

OTHER PUBLICATIONS

First Search Report received Sep. 12, 2023; Chinese Patent Application No. 202080015085.4; 2 pages.
China Patent Office "Office Action", issued in connection with China Patent Application No. 202080015085.4. dated Mar. 13, 2024 (17 pages) (8 pages of English Translation and 9 pages Original Document).

* cited by examiner

DEVICE FOR SUPPORTING AT LEAST ONE ARM OF A USER, AND HEADREST

CROSS-REFERENCE TO RELATED APPLICATIONS

This is a national phase application of International Application No. PCT/EP2020/054372, filed 19 Feb. 2020, which claims the benefit of German Patent Application No. 102019104344.1, filed 20 Feb. 2019, the disclosures of which are incorporated, in their entireties, by this reference.

TECHNICAL FIELD

The invention relates to a device for supporting at least one arm of a user, wherein the device has at least one arm support element with a spacer element and an arm shell for placing on the arm, at least one passive actuator that is configured to apply a force to the one arm support element and at least one counter bearing for the force to be applied, said counter bearing having at least one force transmission element and one counter bearing element, wherein the spacer element is arranged on the at least force transmission element such that it can be swivelled.

BACKGROUND

Such a device is known, for example, from WO 2018/224555 A1 and is used in particular to support the user if they have to raise their arms for a long time, for example to work above their head. A similar device is known from US 2016/0081871 A1. It features a counter bearing element designed in the form of a strap that can be placed around the user's torso; two support braces run along the user's back to their shoulder, each of said support braces being connected to a joint above and laterally next to the shoulder of the user, so that the arm can be raised. Spring elements that are positioned on the joints exert an upward force on the arm shells so that the arms are supported, for example, when heavy objects are lifted. If the arms are lowered, a pressure must be exerted by the arms onto the arm shells, wherein this pressure exceeds the force applied by the spring elements.

In particular for work carried out above one's head, but also in other situations in which a user's arms must be raised, such devices do an effective job of supporting the arms. However, the user's gaze normally follows their hands to see and observe what work is being carried out and what needs to be done next. This means that the user's head is moved into the neck to be able to look upwards. Particularly if this position has to be assumed for a long time, it may cause tension in the neck area and the back of the head, which can be unpleasant and painful, and can result in further postural damage and impairment of the user.

SUMMARY

The invention thus aims to further develop a device according to the preamble of claim 1 so that these disadvantages are eliminated.

The invention solves the problem with a device according to the preamble of claim 1, which is characterized in that the device features a headrest with at least one shoulder element and at least one support element that is arranged on the at least one shoulder element such that it can be detached and is elastic, the headrest being designed in such a way that, when the device is mounted, it supports the user's head when the head is tilted backwards at least by a predetermined limit angle.

According to the invention, the headrest of the device thus has at least one shoulder element that is arranged on the user's shoulder. This may be, for example, one or multiple brackets that are placed across the shoulders and are designed essentially as a U that is open at the bottom. At least one bracket preferably extends across each of the two shoulders of the user, wherein these two brackets are preferably connected to each other ventrally, i.e. at the front, and/or dorsally, i.e. at the back. In an especially preferred embodiment, the at least one shoulder element is a frame that extends around the head and features two U-shaped elements, which are open at the bottom, on the shoulders, said elements being connected to each other both ventrally and dorsally.

According to the invention, the at least one support element is arranged on the at least one shoulder element such that it can be detached. As a result, the support element, for example, can be easily removed from the shoulder element and exchanged for a different support element, for example, that has different geometric dimensions in a preferred embodiment. This allows different shoulder elements and different support elements to be combined with each other in order to combine shoulder element and support element dimensions that are suitable for the respective user. This is achieved, for example, by way of positive-locking elements that are arranged on the at least one shoulder element and the at least one support element such that they correspond to each other. Such positive-locking elements may be, for example, velcro elements, press studs, snap or clip elements, or other positive-locking elements.

Preferably, the support element extends dorsally, i.e. at the back, upwards from the at least one shoulder element towards the head. According to the invention, it is designed to be elastic. Here, the elasticity refers particularly to the fact that the support element for the head does not form a fixed and immovable end stop against which the head strikes when tilted backwards. This can be painful, or at least uncomfortable, and can also result in the head being supported, but in a predetermined position that may not be the desired position. If the at least one support element is designed to be elastic, it can yield to the pressure applied by the head to the support element at least in a predetermined range and thus enable the optimum support position for the respective desired working position of the hands or viewing direction of the head.

In a preferred embodiment, the device features a plurality of differently configured support elements that can be designed, for example, to be of different lengths, so that they extend upwards from the at least one element to different extents when connected to the at least one shoulder element. This enables the limit angle at which the support element comes into contact with the backwards-tilted head to be adjusted and changed. The limit angle preferably lies between 5° and 45°, preferably between 10° and 30°, especially preferably between 15° and 25°, most preferably at 20°. This refers to the angle about which the head of the user of the device must be tilted out of the upright position in order to come into contact with the support element or another component of the headrest. From this point onwards, i.e. from when the limit angle is reached, the elasticity of the headrest preferably allows the head to be tilted further by at least 5°, preferably at least 10°, especially preferably at least 15°, and by at most 30°, preferably at most 25°, especially preferably at most 20°.

In a preferred embodiment, the support element also allows the user to rotate their head when the head is resting on the support element. In this case, the support element can be configured in such a way that it slides along the back of the head when the head is being rotated, without the position in which the support element is resting on the head remaining fixed and constant, and the elasticity of the support element allows a movement of the head, such that it becomes deformed in the process.

The at least one support element can preferably be fixed to the at least one shoulder element in multiple positions, which are preferably infinitely adjustable. This renders it possible to take the individual dimensions and proportions of the respective user into account. This is especially easy to achieve when the at least one support element is arranged on the at least one shoulder element by means of velcro fasteners. This makes it particularly easy to achieve infinite adjustability.

In a preferred embodiment, there is at least one head support element on the at least one support element for resting against the user's head, said head support element preferably adapting to a contour of the head when it comes into contact with the user's head. Such a head support element may be designed as a pillow, for example, and preferably made of a foam material that is—particularly preferably—covered with a fabric cover made of a textile material. It is particularly preferable for such a head support element to be arranged on the support element such that it can be detached, for example, for cleaning or repair purposes or, for example, when the user is different, and replaced by a different head support element.

It is especially preferable if the at least one support element features at least two head support elements that rest on the user's head, preferably in the region of the superior nuchal line, i.e. the upper neckline, the inferior nuchal lie, i.e. the lower neckline, particularly preferably laterally to the external occipital protuberance.

It is particularly preferable for the at least one head support element to feature a flat, flexible, preferably elastic material, or to be composed of such a material, and to preferably be arranged on the support element in such a way that there is a gap between the head support element and the support element that is not closed when the device is used as intended. This construction can also be considered and described as a "hammock", with the actual head support element forming the hammock and the support element forming the corresponding support structure. The head support element is connected to the at least one support element at the edge at two or more points, if necessary at the complete circumferential edge, in such a way that it is stretched between the fixing points or is at least arranged in such a way that it does not come into contact with the support element between the contact points. If the user's head is now tilted backwards by at least the predetermined limit angle, it comes into contact with the head support element which, thanks to the hammock structure and arrangement, can optimally adapt to the shape of the user's head. This occurs irrespectively of whether the head is tilted straight backwards, i.e. the direction of vision continues to point forward, or, in addition to being tilted backwards, the head is rotated to the right or left. Due to the hammock-like structure, this adaptation is always optimal. The fact that the gap between the at least one head support element and the at least one support element is not closed as a result of the forces that occur when the device is used as intended ensures an effective cushioning of the head, as it does not come into contact with the actual support element, even in the supported state.

The head support preferably comprises at least one strap, preferably at least two straps, that can be or are fixed to the counter bearing, preferably to the counter bearing element. As a result, the position of the headrest on the user's body is secured, even when it is subjected to a load, i.e. when the user's head is tilted backwards. The at least one strap is positioned on the counter bearing, preferably the counter bearing element, in particular a hip strap, via, for example, positive-locking elements, such as clips or snap elements, or via clasp elements.

In a preferred embodiment, the at least one strap extends ventrally, i.e. at the front, on the user's body when the device is mounted. This configuration is especially beneficial because the head tilted backwards exerts a force on the neck support which can be transferred particularly well, simply and safely to the counter-bearing element, preferably the hip strap, by means of straps running along the front of the body. In addition, this design of the at least one strap renders the device and in particular the headrest especially easy to mount, as the at least one strap must be fastened to the counter bearing element at the front of the body.

Alternatively or additionally, the at least one strap can extend dorsally on the user's body when the device is mounted. This is particularly advantageous if, for example, sufficient stability of the position of the head on the user's body is ensured by way of the at least one shoulder element.

At least one of the straps preferably comprises a positive-locking element, in particular a snap element and/or a clip element, wherein the strap can be fixed to the counter bearing by engaging the positive-locking element with a corresponding counter element.

The elasticity of the support element can preferably be adjusted. This may be achieved, for example, with additional reinforcement elements that can be arranged on an elastic brace or an elastic component of the support element, thereby increasing, for instance, the wall thickness such that the elasticity decreases. Alternatively or additionally, the at least one support element itself may be composed of multiple components that can be positioned relative to one another in different orientations or with differently sized contact surfaces. Elasticity can also be adjusted in this manner.

The at least one shoulder element is preferably designed to be elastic. This is advantageous, for example, if it is geometric in form, said form being expanded when placed on the user's shoulder. This creates a clamping effect that renders a slipping of the shoulder element relative to the user's body at least more difficult, but preferably entirely impossible.

The invention also solves the problem with a headrest with at least one shoulder element and at least one support element that is arranged on the at least one shoulder element such that it can be detached and is elastic, the headrest being designed in such a way that, when the device is mounted, it supports the user's head if the head is tilted backwards at least by a predetermined limit angle. Such a headrest is particularly well-suited for the type of device described here.

Preferably, the headrest has at least one strap that features at least one fastening element, in particular a positive-locking element, by means of which the at least one strap can be fixed to a counter bearing, which is preferably a hip strap, and/or in that the at least one shoulder element is not made of a flexible material. Otherwise, the shoulder element could also be designed as a strap or pair of straps, for example.

BRIEF DESCRIPTION OF THE DRAWINGS

In the following, some examples of embodiments of the present invention will be explained in more detail by way of the attached figures: They show.

DETAILED DESCRIPTION

Figure 1:
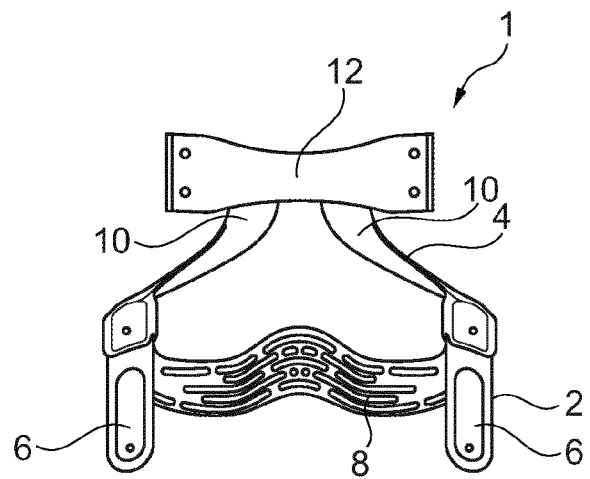
FIGS. 1 to 4—various representations of a headrest according to a first example of an embodiment of the present invention, FIGS. 5 to 8—the representations from FIGS. 1 to 4 for a second example of an embodiment of the present invention, FIGS. 9 and 10—two representations of a headrest according to another example of an embodiment of the present invention, FIGS. 11 and 12—two representations of a headrest according to another example of an embodiment, FIGS. 13 to 15—detailed representations of a headrest according to another example of an embodiment of the present invention, and FIGS. 16 and 17—two representations of a device according to an example of an embodiment of the present invention.

FIG. 1 depicts a headrest 1 that features a shoulder element 2 and a support element 4. The shoulder element 2 comprises two shoulder brackets 6 that are placed across the user's shoulders when the headrest 1 is mounted. They are dorsally connected to each other, i.e. in the back region, by a connecting brace 8. The support element 4 is situated on the shoulder element 2, the former comprising two support brackets 10 in the example of embodiment shown; one of the two shoulder brackets 6 extends upwards from each of these support brackets. They are connected to each other in the upper region by a head support element 12, on which the user's head rests.

Figure 2:
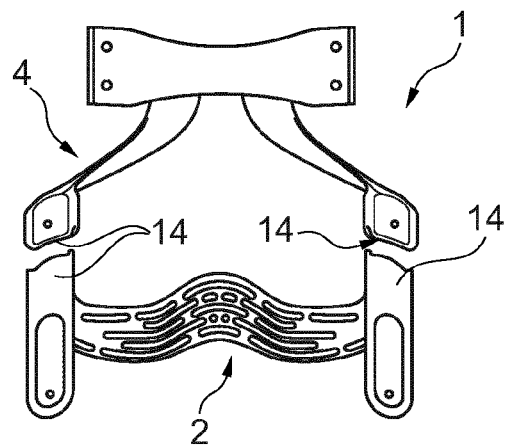

FIG. 2 depicts the representation from FIG. 1 with separated components. The shoulder element 2 has been separated from the support element 4. Both feature velcro fastening elements 14, by means of which the two components can be fixed in different positions that are infinitely adjustable.

Figure 3:
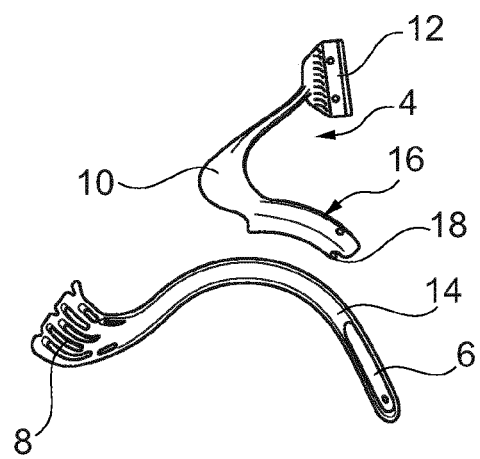
Figure 4:
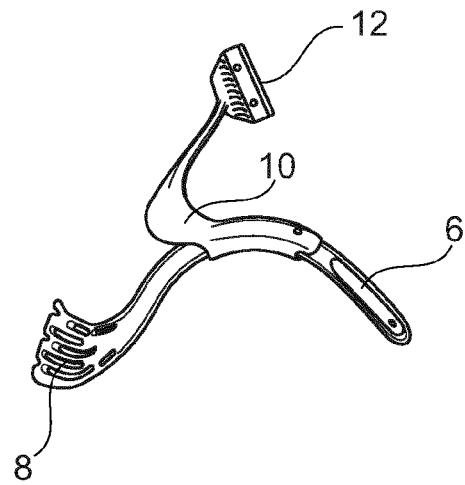
Figure 5:
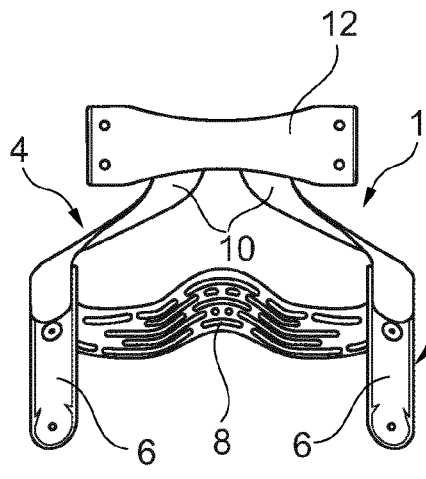

FIG. 3 depicts a side view of the representation from FIG. 2. One of the shoulder brackets 6 can be seen where the velcro fastener element 14 is located. It is connected in the back area to the second shoulder bracket 6, not depicted in FIG. 3, by the connecting brace 8. The support element 4, on which the head support element 12 is arranged, features the two support brackets 10, of which only one is shown. In one contact area 16, in which the support bracket 10 comes into contact with the respective shoulder bracket 6, the support bracket 10 features a rail 18 that is configured to at least partially surround the respective shoulder bracket 6. The velcro fastener elements 14 are still in position so as to increase the holding force between the support element 4 and the shoulder element 2. FIG. 4 depicts a side view of the representation from FIG. 1. It once again shows one of the shoulder brackets 6, one of the support brackets 10 with the head support element 12 arranged on it and the connecting brace 8, which connects the two shoulder brackets 6 to one another.

Figure 6:
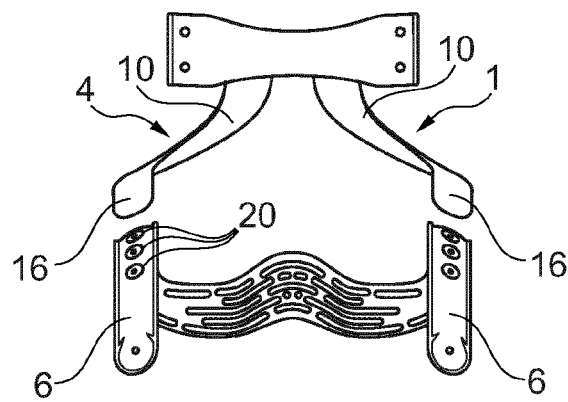
Figure 7:
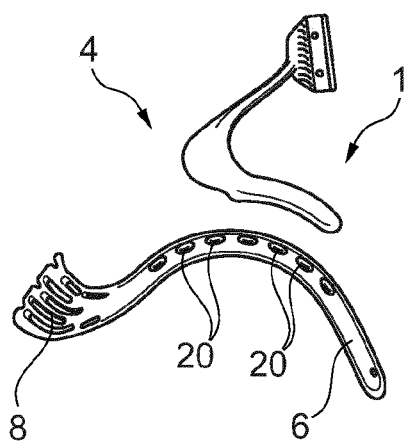
Figure 8:
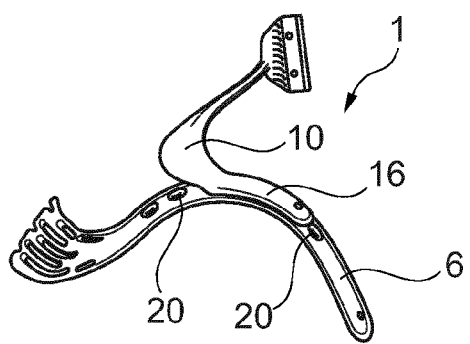

FIGS. 5 to 8 show a further example of an embodiment of the headrest 1. It also comprises the shoulder element 2 with the two shoulder brackets 6, which are connected to each other by the connecting brace 8. The support element 4 again shows the two support brackets 10, the head support element 12 being located in the upper region of said support brackets such that there is a gap 50 between the head support element 12 and the support element 4. However, unlike the embodiment from FIGS. 1 to 4, the support element 4 is arranged on the shoulder element 2 via press studs, which is shown in FIG. 6 in particular. The corresponding positive-locking elements 20 can be seen, which are positioned on the shoulder brackets 6 and can engage with counter elements that are arranged on the underside of the contact area 16 of the respective support bracket 10, but are not depicted in the figures. In this way, the position of the shoulder element 2 relative to the support element 4 can be changed, but not infinitely, as is the case with velcro fasteners. FIGS. 7 and 8 show the lateral representation. In FIG. 7, the shoulder bracket 6 with the connecting brace 8 is shown detached from the support element 4. The positive-locking elements 20 arranged on the shoulder bracket 6 can be clearly seen. FIG. 8 shows the representation in the connected position. Here, some of the positive-locking elements are still visible, while the contact area 16 of the support bracket 10 has been brought into contact with the shoulder bracket 6.

Figure 9:
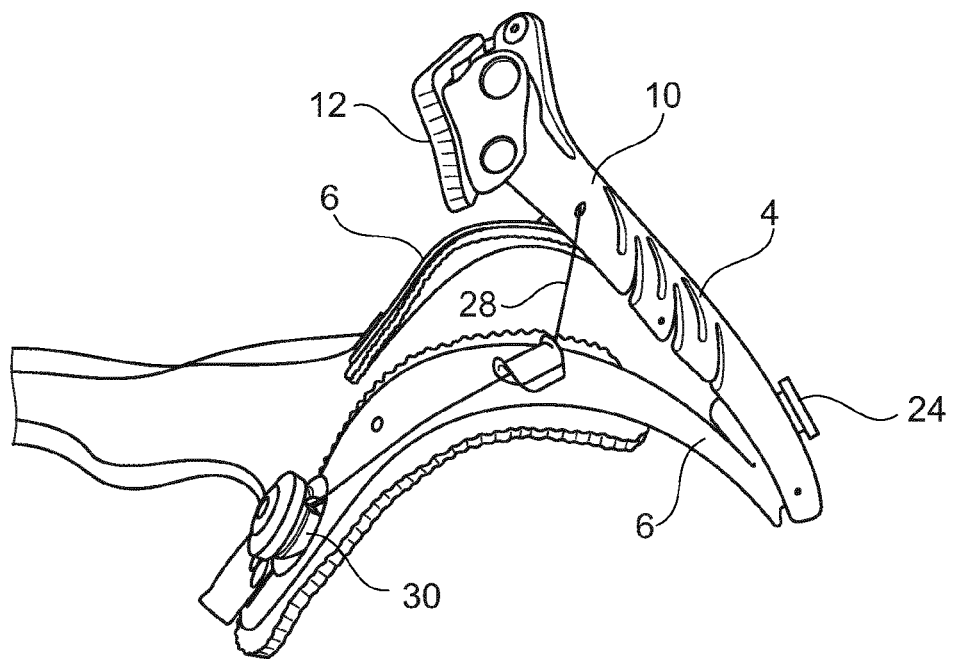
Figure 10:
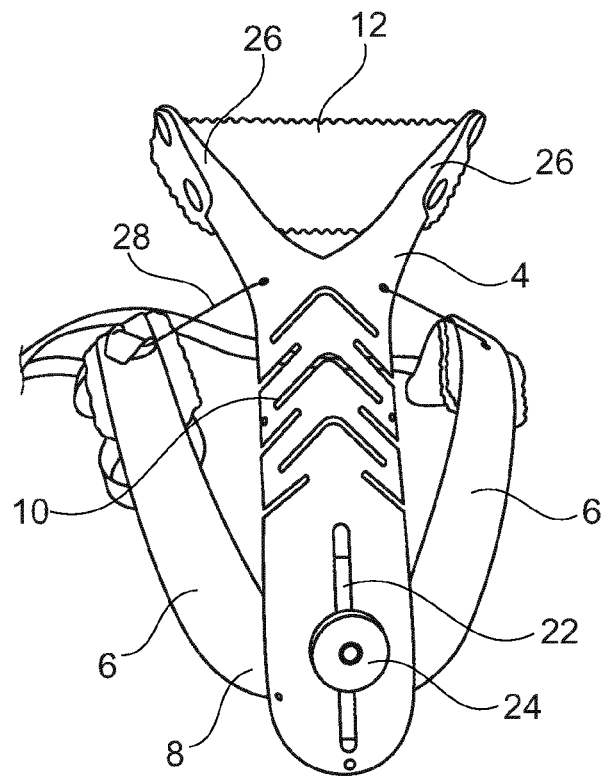

FIGS. 9 and 10 show a different embodiment. It features two shoulder brackets 6 that are made of a solid yet elastic plastic and placed across the wearer's shoulders. They are connected to each other in the back area by a short connecting brace 8 on which the support element 4 is arranged. There is an elongated hole 22 in the support element 4 through which a screw 24 is guided; this screw is connected to the connecting brace 8 of the two shoulder brackets 6. A bore is situated in the connecting brace 8, said bore having an inner thread in which the screw 24 engages. If the screw 24 is loosened, the support element 4 can be displaced along the elongated hole 22 relative to the shoulder brackets 6 and thus relative to the shoulder element 2. Once the desired position has been reached, the screw 24 is tightened and a further displacement is not possible.

The support element 4 has only one support bracket 10, which features a number of recesses and openings, thereby achieving the elasticity of the support bracket 10. The upper end of the support bracket 10 features two projections 26 that are spaced apart either in a U-shape or a V-shape. The actual head support element, designed here as a textile element, is arranged between them.

The embodiment from FIGS. 9 and 10 also has a tensioning device 28, designed in the form of a wire or band, that can be wound up and unwound using a corresponding tensioning element 30. This changes the effective length of the tensioning device, so that the upper end of the support brace 10 can be pulled down or released back up. As a result, the position at which the head support element 12 comes into contact with a head changes.

Figure 11:
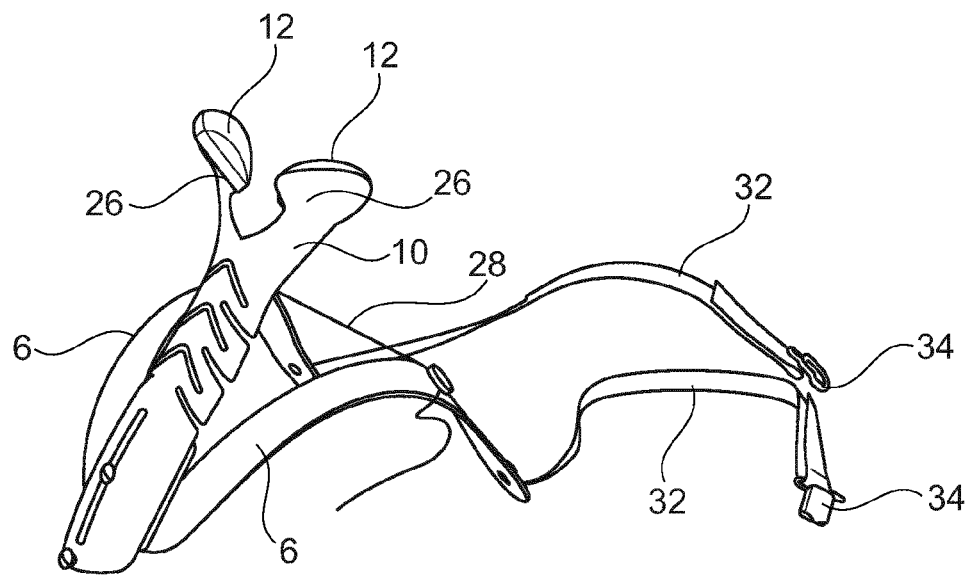
Figure 12:
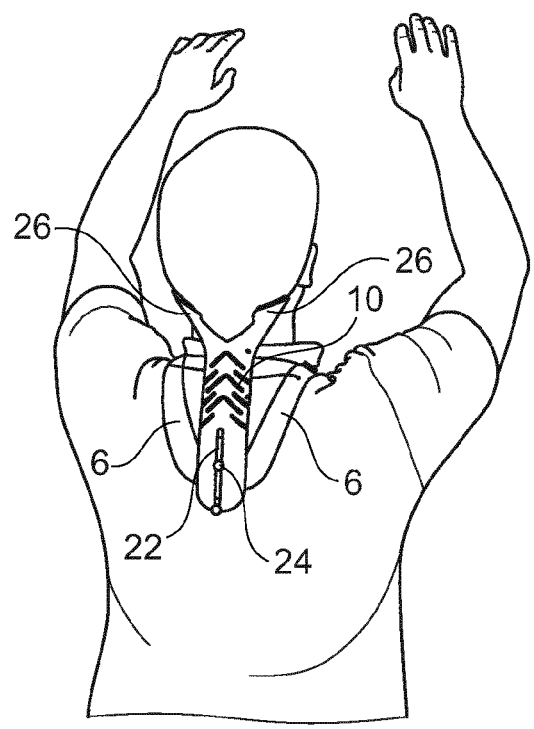

FIGS. 11 and 12 depict a further embodiment, wherein FIG. 12 depicts it in the mounted state. It also comprises two shoulder brackets 6 that are connected to each other in the dorsal region. The single support bracket 10 is again arranged in this region, said bracket featuring an elongated hole 22 in which a screw 24 is arranged. This support bracket 10 also features a number of recesses and bores, by way of which the elasticity of an already elastic material is further increased.

In the upper area of the support bracket 10, it also splits into two projections 26, on which two head support elements 12 are now arranged, unlike in FIGS. 9 and 10. FIG. 12 depicts the device shown in FIG. 8 in the mounted state: it can be seen that the head support elements 26 rest on the head in the rear skull region.

FIG. 11 shows that this headrest 1 also features a tensioning device 28 that has the effect previously described in reference to FIGS. 9 and 10. In addition, the device has two straps 32 with a fastening element 34 located on the ends facing away from the headrest. In the example of the embodiment shown, these are clamping buckles as known, for example, from a pair of braces. These fastening elements 34 render it possible to fix the straps 32 and thus the entire headrest 1 to a counter bearing element, for example a hip strap or belt.

Figure 13:
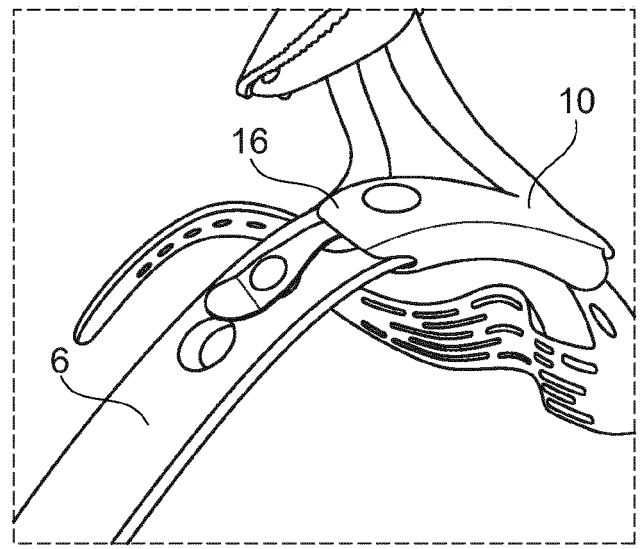
Figure 14:
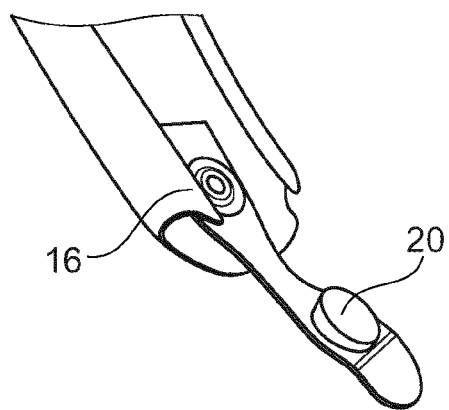
Figure 15:
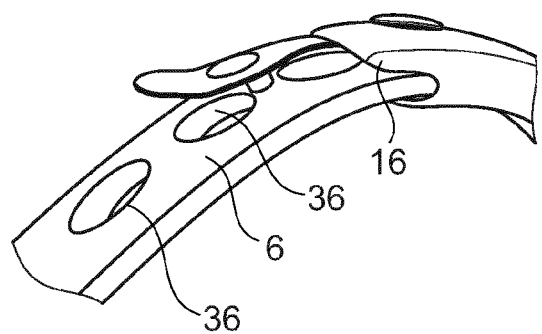

FIGS. 13 to 15 depict details of the connecting device between the shoulder bracket 6 and the contact area 16 of the support bracket 10. The shoulder brackets 6 feature recesses 36 through which the corresponding positive-locking elements, which are arranged at the front end of the contact area 16 of the support bracket 10, can be guided. Such a positive-locking element 20 is shown in FIG. 14 in particular. This enables the support bracket 10 to be fixed in different positions on the shoulder bracket 6.

Figure 16:
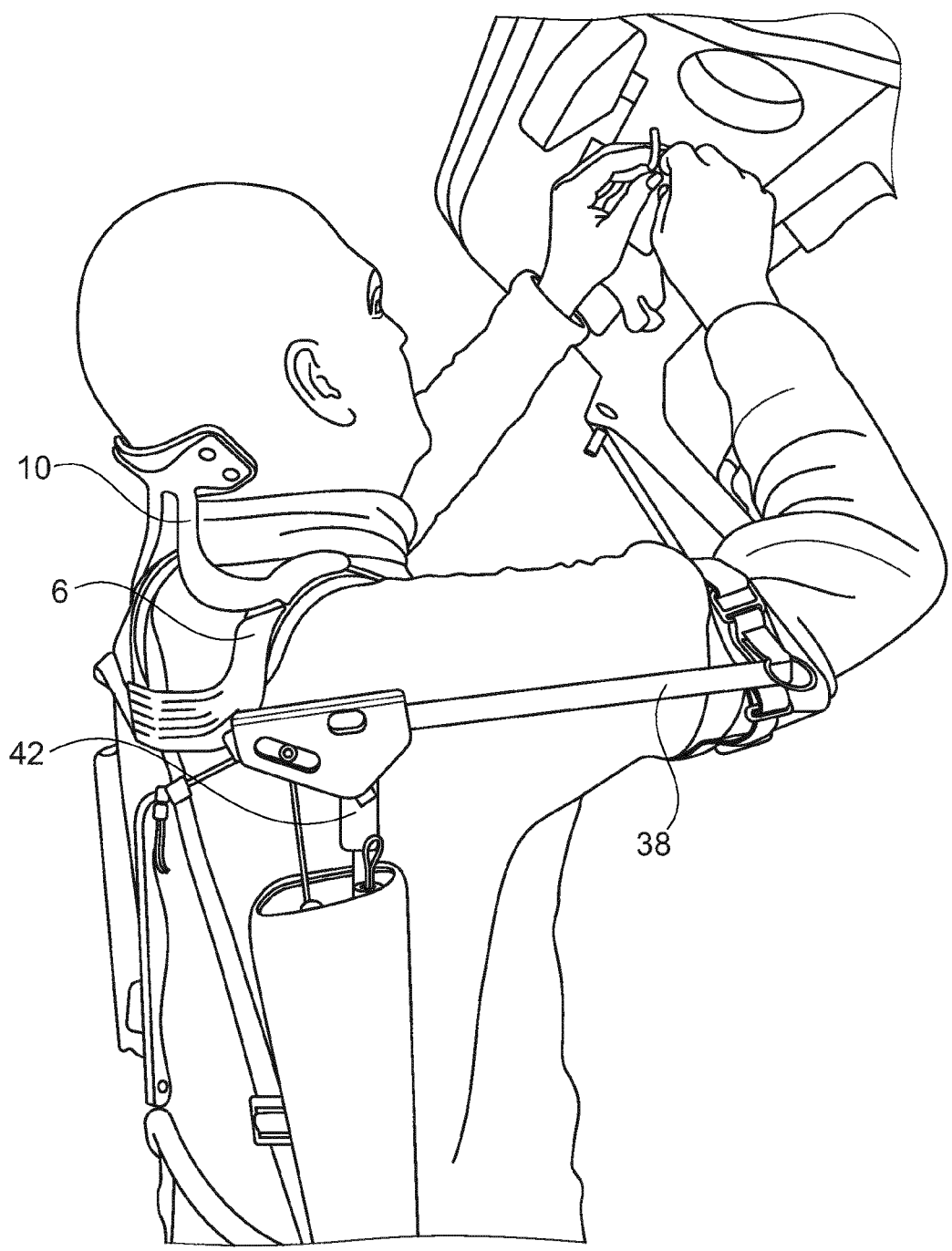
Figure 17:
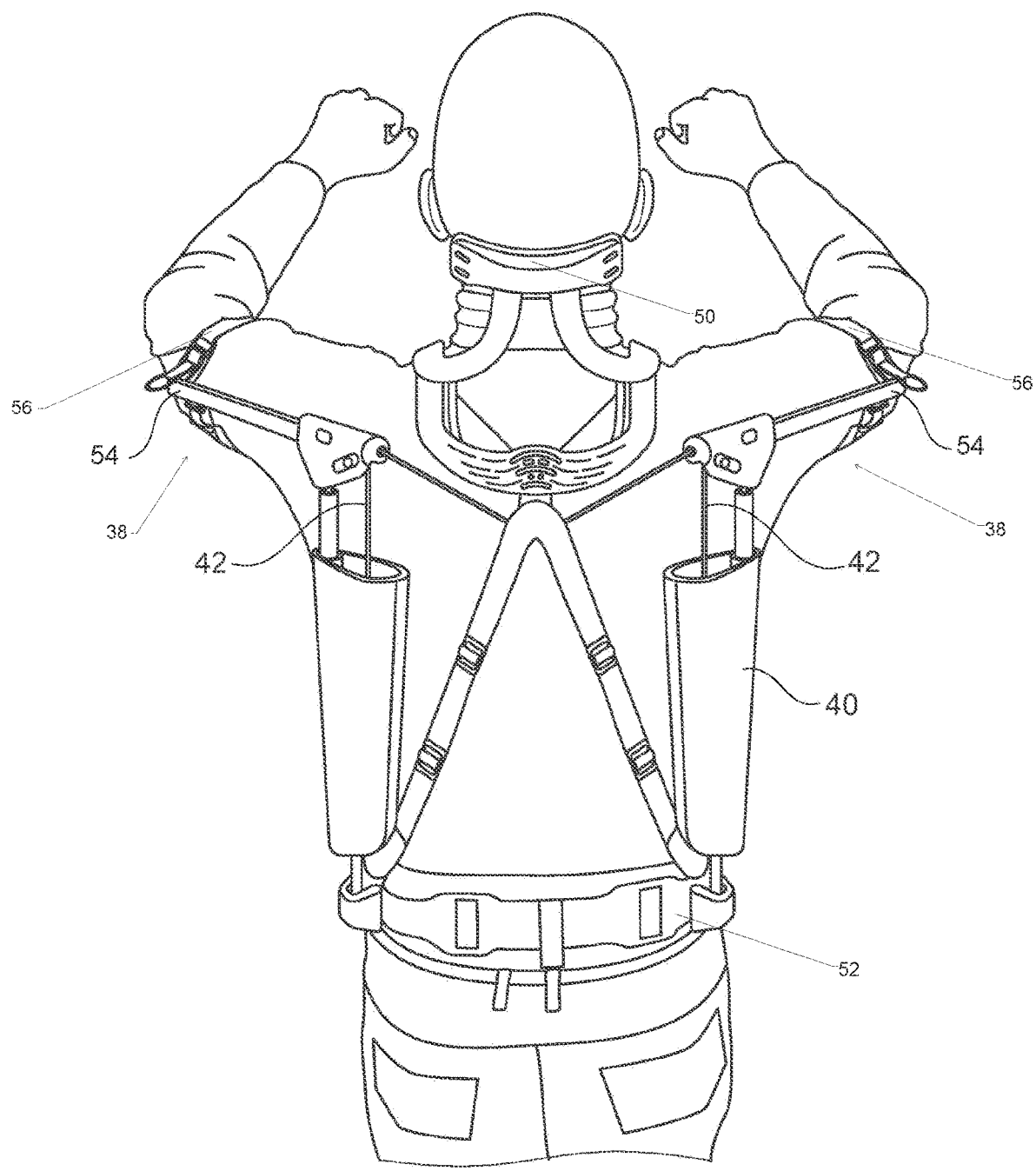

FIGS. 16 and 17 depict a device for supporting two arms in the mounted state. It comprises two arm support elements 38, each of which is connected to a force transmission element 40. They each have a passive actuator 42 and a counter bearing element 44 in the form of a hip strap 52. The two arm support elements 38 each include a spacer element 54 and an arm shell 56 for mounting on an upper arm portion of the arm of the user.

The headrest with the shoulder element 2, its two shoulder brackets 6 and the support element 4 with the support brackets 10 also constitute part of the device.

REFERENCE LIST 1 headrest
2 shoulder element
4 support element
6 shoulder bracket
8 connecting brace
10 support bracket
12 head support element
14 velcro element
16 contact area
18 rail
20 positive-locking element
22 elongated hole
24 screw
26 projection
28 tensioning device
30 tensioning element
32 strap
34 fastening element
36 recess
38 arm support element
40 force transmission element
42 passive actuator
44 counter bearing element

The invention claimed is:

1. A device for supporting at least one arm of a user, wherein the device comprises:
at least one arm support element with a spacer element and an arm shell for mounting on an upper arm portion of the arm of the user,
at least one passive actuator, which is configured to apply a force to the at least one arm support element, and
at least one counter bearing which comprises at least one force transmission element and a counter bearing element,
wherein the spacer element is arranged on the at least one force transmission element such that it can be swivelled, and wherein the device has a headrest with at least one shoulder element and at least one support element that is arranged on the at least one shoulder element such that it can be detached and is elastic, wherein the at least one support element comprises two elastic support brackets, wherein the headrest further comprises at least one head support element arranged on the two elastic support brackets, wherein the at least one head support element comprises an elastic material and is arranged on the at least one support element in such a way that there is a gap between the at least one head support element and the at least one support element that is not closed when the device is used as intended, and wherein the elastic material of the at least one head support element and the gap are configured such that the at least one head support element adapts to the user's head when the user's head is rotated to the user's right and left,
wherein the headrest is designed in such a way that, when the device is mounted, the headrest supports the user's head when the user's head is tilted backwards at least by a predetermined limit angle.

2. The device according to claim 1, wherein the head support comprises at least one strap fixed to the at least one counter bearing.

3. The device according to claim 2, wherein the at least one strap extends ventrally on the user's body when the device is mounted.

4. The device according to claim 2, wherein the at least one strap extends dorsally on the user's body when the device is mounted.

5. The device according to claim 2, wherein at least one of the straps comprises a positive-locking element comprising a snap element or a clip element, wherein the strap is fixed to the at least one counter bearing by engaging the positive-locking element with a corresponding counter element.

6. The device according to claim 1, wherein the at least one support element can be fixed on the at least one shoulder element in multiple positions.

7. The device according to claim 1, wherein the at least one head support element is configured to adapt to a contour of the user's head when the at least one head support element comes into contact with the user's head.

8. The device according to claim 1, wherein an elasticity of the at least one support element is adjustable.

9. The device according to claim 1, wherein the at least one shoulder element is designed to be elastic.

10. The device according to claim 1, wherein the headrest has at least one strap comprising at least one fastening element that fixes the at least one strap to the at least one counter bearing, wherein the at least one counter bearing comprises a hip strap, and wherein the at least one shoulder element is not made of a flexible material.

11. The device according to claim 1, wherein an elasticity of the at least one support element is adjustable.

12. A device for supporting at least one arm of a user comprising:
at least one arm support element with a spacer element and an arm shell for mounting on an upper arm portion of the arm of the user;
at least one passive actuator configured to apply a force to the at least one arm support element;

at least one counter bearing, the at least one counter bearing including at least one force transmission element and a counter bearing element; and wherein the spacer element is arranged on the at least one force transmission element such that it can be swivelled, and wherein the device has a headrest with at least one shoulder element and at least one support element that is arranged on the at least one shoulder element such that it can be detached and is elastic, wherein the at least one support element comprises two elastic support brackets;

wherein the device further comprises at least one head support element arranged on the two elastic support brackets, such that there is a gap between the at least one head support element and the at least one support element, wherein the at least one head support element comprises an elastic material and is arranged on the at least one support element in such a way that the gap is not closed when the device is used as intended, and wherein the elastic material of the at least one head support element and the gap are configured such that the at least one head support element adapts to the user's head when the user's head is rotated to the user's right and left;

and wherein the headrest is designed in such a way that, when the device is mounted, it supports the user's head when the user's head is tilted backwards at least by a predetermined limit angle.

13. The device according to claim 12, wherein the at least one head support element comprises at least one strap that can be fixed to the counter bearing.

14. The device according to claim 13, wherein the at least one strap extends ventrally on the user's body when the device is mounted.

15. The device according to claim 13 wherein the at least one strap extends dorsally on the user's body when the device is mounted.

16. The device according to claim 13, wherein the at least one strap comprises a positive-locking element, wherein the at least one strap can be fixed to the at least one counter bearing by engaging the positive-locking element with a corresponding counter element.

17. The device according to claim 12, wherein the at least one head support element is composed of a flat, flexible, or elastic material.

18. A device for supporting at least one arm of a user comprising:

at least one arm support element with a spacer element and an arm shell for mounting on an upper arm portion of the arm of the user;

at least one passive actuator configured to apply a force to the at least one arm support element;

at least one counter bearing, the counter bearing including at least one force transmission element and a counter bearing element; and wherein the spacer element is arranged on the at least one force transmission element such that it can be swivelled, and wherein the device has a headrest with at least one shoulder element and at least one support element that is arranged on the at least one shoulder element such that it can be detached and is elastic, wherein the at least one support element comprises two elastic support brackets;

wherein the device further comprises at least one head support element arranged on the at least one support element, such that there is a gap between the at least one head support element and the at least one support element, the head support including at least one strap that can be fixed to the counter bearing, wherein the at least one head support element comprises an elastic material and is arranged on the at least one support element in such a way that the gap is not closed when the device is used as intended, and wherein the elastic material of the at least one head support element and the gap are configured such that the at least one head support element adapts to the user's head when the user's head is rotated to the user's right and left; and wherein the headrest is designed in such a way that, when the device is mounted, it supports the user's head when the user's head is tilted backwards at least by a predetermined limit angle.

* * * * *